(12) United States Patent
Haldavanekar et al.

(10) Patent No.: US 9,029,421 B2
(45) Date of Patent: May 12, 2015

(54) PROCESS FOR THE SYNTHESIS OF ARFORMOTEROL

(75) Inventors: Vaishali Vaman Haldavanekar, Mumbai (IN); Mangesh Prabhu, Mumbai (IN); Dharmaraj Ramachandra Rao, Thane (IN); Rajendra Narayanrao Kankan, Mumbai (IN)

(73) Assignee: Cipla Limited, Mumbai (IN)

( * ) Notice: Subject to any disclaimer, the term of this patent is extended or adjusted under 35 U.S.C. 154(b) by 368 days.

(21) Appl. No.: 12/995,016

(22) PCT Filed: Jun. 2, 2009

(86) PCT No.: PCT/GB2009/001373
§ 371 (c)(1),
(2), (4) Date: Feb. 21, 2011

(87) PCT Pub. No.: WO2009/147383
PCT Pub. Date: Dec. 10, 2009

(65) Prior Publication Data
US 2011/0166237 A1    Jul. 7, 2011

(30) Foreign Application Priority Data
Jun. 2, 2008 (IN) .......................... 1172/MUM/2008

(51) Int. Cl.
| | |
|---|---|
| *C07C 217/86* | (2006.01) |
| *C07C 213/02* | (2006.01) |
| *C07C 217/70* | (2006.01) |
| *C07C 213/00* | (2006.01) |
| *C07C 213/08* | (2006.01) |
| *C07C 213/10* | (2006.01) |
| *C07C 231/02* | (2006.01) |
| *C07C 233/43* | (2006.01) |

(52) U.S. Cl.
CPC ............. *C07C 217/86* (2013.01); *C07C 213/00* (2013.01); *C07C 213/08* (2013.01); *C07C213/10* (2013.01); *C07C 231/02* (2013.01); *C07C 233/43* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 3,994,974 A | 11/1976 | Murakami et al. | |
| 6,268,533 B1 * | 7/2001 | Gao et al. ...................... | 564/216 |

FOREIGN PATENT DOCUMENTS

| | | |
|---|---|---|
| GB | 2380996 A | 4/2003 |
| IE | 20000138 | 6/2001 |
| JP | 04026661 A | 1/1992 |
| JP | 08505646 A | 6/1996 |
| JP | 2001503772 A | 3/2001 |
| JP | 2002518468 A | 6/2002 |
| JP | 2002255910 A | 9/2002 |
| WO | 9512572 A1 | 5/1995 |
| WO | 9518094 A1 | 7/1995 |
| WO | 9821175 A1 | 5/1998 |
| WO | 9967198 A1 | 12/1999 |
| WO | WO 2004/099132  * | 11/2004 |
| WO | 2005097731 A2 | 10/2005 |
| WO | 2005113547 A1 | 12/2005 |
| WO | 2008035380 A2 | 3/2008 |
| WO | 2009147383 A1 | 12/2009 |

OTHER PUBLICATIONS

Gomez et al. (Adv. Synth. Catal., 344:1037-1057, 2002).*
Foreign communication from a related counterpart application—International Search Report and Written Opinion, PCT/GB2009/001373, Jul. 23, 2009, 14 pages.
Hett, Robert, et al., "Enantio- and diastereoselective synthesis of all four stereoisomers of formoterol," Tetrahedron Letters, 1997, vol. 38, No. 7, pp. 1125-1128, Elsevier Science Ltd.
Murase, Kiyoshi, et al., "Absolute configurations of four isomers of 3-formamido-4-hydroxy-α-[[N-ρ-methoxy-α-methylphenethyl)amino]methyl]benzyl alcohol, a potent β-adrenoreceptor stimulant," Chemical & Pharmaceutical Bulletin, 1978, vol. 26, No. 4, pp. 1123-1129, Pharmaceutical Society of Japan.
Trofast, Jan, et al., "Steric aspects of agonism and antagonism at β-adrenoceptors: synthesis of and pharmacological experiments with the enantiomers of formoterol and their diastereomers," Chirality, 1991, No. 3, pp. 443-450, XP-002057060.
Foreign communication from the priority application—International Preliminary Report on Patentability, PCT/GB2009/001373, Dec. 6, 2010, 7 pages.

* cited by examiner

*Primary Examiner* — Bong-Sook Baek
(74) *Attorney, Agent, or Firm* — Conley Rose, P.C.; Rodney B. Carroll

(57) ABSTRACT

The present invention provides a process for preparing a compound of formula (VI) or a salt thereof, the process comprising: (i) reacting 4-methoxyphenyl acetone with an amine of formula (VIII) under conditions of reductive amination to produce a compound of formula (II) or a salt thereof, wherein there is no isolation of an imine intermediate formed during the reductive amination; (ii) condensing the compound (II) or the acid addition salt thereof with an α-haloketone of formula (III) to produce the compound of formula (IV); (iii) reducing the compound (IV) to a compound of formula (V); and (iv) reducing the compound (V) to the compound of formula (VI), wherein the reduction is carried out in the presence of either (1) a hydrogen donating compound in the presence of a hydrogen transfer catalyst; or (2) ammonium formate using a hydrogenation catalyst, wherein $R_1$ and $R_2$ are independently optionally substituted arylalkyl, and Hal is selected from chloro or bromo.

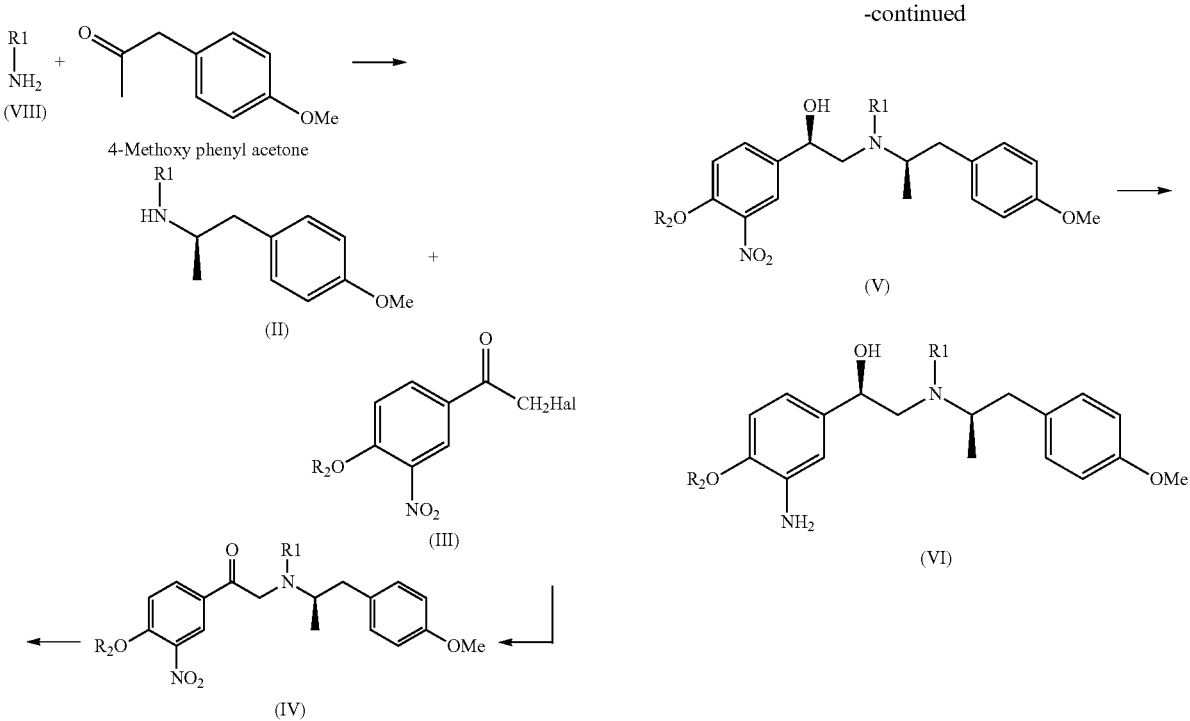
18 Claims, No Drawings

PROCESS FOR THE SYNTHESIS OF ARFORMOTEROL

CROSS-REFERENCE TO RELATED APPLICATIONS

This application is a filing under 35 U.S.C. 371 of International Application No. PCT/GB2009/001373 filed Jun. 2, 2009, entitled "Process for the Synthesis of Arformoterol," claiming priority of Indian Patent Application No. 1172/MUM/2008 filed Jun. 2, 2008, which applications are incorporated by reference herein in their entirety.

FIELD OF INVENTION

The present invention relates to a process for the preparation of intermediates useful in the synthesis of formoterol or enantiomers and acid addition salts thereof.

BACKGROUND OF THE INVENTION

Formoterol is a long-acting $\beta_2$-adrenoceptor agonist and has a long duration of action of up to 12 hours. Chemically it is termed as N-[2-hydroxy-5-[1-hydroxy-2-[[2-(4-methoxyphenyl)propan-2-yl]amino]ethyl]phenyl]-formamide. The structure of formoterol is as shown below.

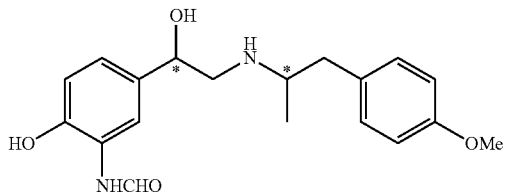

The asterisks indicate that formoterol has two chiral centers in the molecule, each of which can exist in two possible configurations. This gives rise to four diastereomers which have the following configurations: (R,R), (S,S), (S,R) and (R,S).

(R,R) and (S,S) are mirror images of each other and are therefore enantiomers. Similarly (S,R) and (R,S) form other enantiomeric pair.

The commercially-available formoterol is a 50:50 mixture of the (R,R)- and (S,S)-enantiomers. (R,R)-formoterol is an extremely potent full agonist at the $\beta_2$-adrenoceptor and is responsible for bronchodilation and has anti-inflammatory properties. On the other hand (S,S)-enantiomer, has no bronchodilatory activity and is proinflammatory.

Murase et al. [Chem. Pharm. Bull., 26(4)1123-1129 (1978)] synthesized all four isomers of formoterol and examined for $\beta$-stimulant activity. In the process, racemic formoterol was subjected to optical resolution with tartaric acid.

In another attempt by Trofast et al. [Chirality, 3:443-450 (1991)], racemic 4-benzyloxy-3-nitrostyrene oxide was coupled with optically pure N—[(R)-1-phenylethyl]-2-(4-methoxyphenyl)-(R)1-methylethylamine to give diastereomeric mixtures of intermediates, which were separated by column chromatography and converted to the optically pure formoterol.

In yet another attempt, racemic formoterol was subjected to separation by using a chiral compound [International publication WO 1995/018094].

WO 1998/21175 discloses a process for preparing optically pure formoterol using optically pure intermediates (R)—N-benzyl-2-(4-methoxyphenyl)-1-methylethyl amine and (R)-4-benzyloxy-3-formamidostyrene oxide.

Preparation of optically pure formoterol is also disclosed in IE 20000138 and GB 2380996.

Increasing use and therapeutic benefit and use through newer drug delivery, Metered Dose Inhaler (MDI) necessitates further research to develop new improved processes for the synthesis of formoterol which are suitable for industrial scale up with improved impurity profile.

OBJECTS OF THE INVENTION

The object of the present invention is to provide a process for preparing intermediates useful in the synthesis of formoterol, its enantiomers and acid addition salts thereof, which process is simple, economical, and suitable for industrial scale up.

Another object of the present invention is to provide an improved process for the synthesis of formoterol, its enantiomers and acid addition salts thereof.

BRIEF SUMMARY OF THE INVENTION

According to a particularly preferred embodiment of the present invention, there is provided a process for preparing the (R,R)-diastereomer of a compound of formula (VI) or a salt thereof,

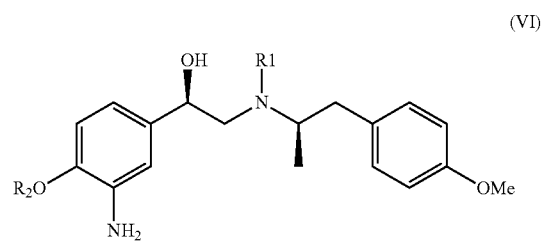

the process comprising: (i) reacting 4-methoxyphenyl acetone with an amine of formula (VIII) under conditions of reductive amination to produce the (R)-enantiomer of a compound of formula (II) or a salt thereof, wherein there is no isolation of an imine intermediate formed during the reductive amination,

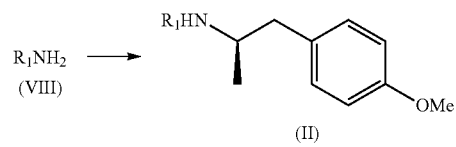

(ii) condensing the (R)-enantiomer of compound (II) or the acid addition salt thereof with an α-haloketone of formula (III) to produce the (R)-enantiomer of a compound of formula (IV);

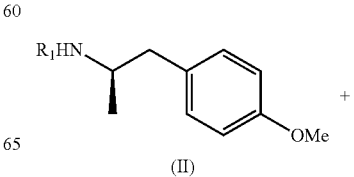

-continued

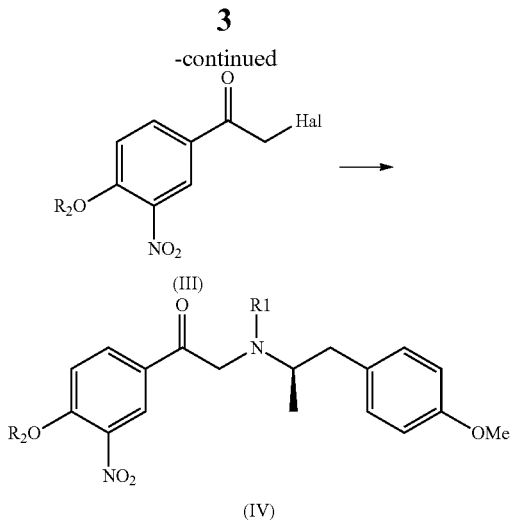

(iii) reducing the (R)-enantiomer of compound (IV) to the (R,R)-diastereomer of a compound of formula (V);

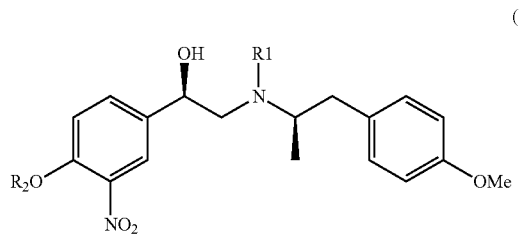

and (iv) reducing the (R,R)-diastereomer of compound (V) to the (R,R)-diastereomer of the compound of formula (VI), wherein the reduction is carried out in the presence of either (1) a hydrogen donating compound in the presence of a hydrogen transfer catalyst; or (2) ammonium formate using a hydrogenation catalyst, wherein $R_1$ and $R_2$ are independently optionally substituted arylalkyl, and Hal is selected from chloro or bromo.

Each of steps (i), (ii), (iii) and (iv) forms an individual aspect of the present invention as is detailed below. The embodiments of the invention, as detailed below, also apply to the preferred process described above.

According to a first aspect of the present invention, there is provided a process for preparing the (R)- or (S)-enantiomer of a compound of formula (II) or an acid addition salt thereof,

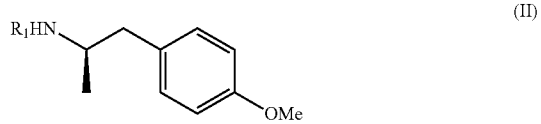

the process comprising reductive amination of 4-methoxyphenyl acetone with an amine of formula (VIII), $$R_1NH_2 \quad (VIII)$$

wherein $R_1$ is optionally substituted arylalkyl to obtain compound (II) or an acid addition salt thereof.

The reductive amination proceeds via an intermediate imine. In the prior art processes (for example, WO 99/67198), the imine is isolated and then hydrogenated. Advantageously, in the process of the present invention, the imine is not isolated, i.e., it is produced in situ.

$R_1$ and $R_2$ function as protecting groups. If $R_1$ and/or $R_2$ are substituted arylalkyl, they may comprise one or more substituents, none of which interferes with the function of the $R_1$ and/or $R_2$ groups as protecting groups. The substituent(s) may be on the aryl component and/or on the alkyl component. In an embodiment, the substituent is on the alkyl component and is $C_{1-3}$ alkyl, preferably methyl.

$R_1$ and $R_2$ are independently an optionally substituted arylalkyl, which means that the alkyl group is covalently bonded to the aryl group and to the nitrogen of the amine moiety (in the case of $R_1$) and to the oxygen of the hydroxyl moiety (in the case of $R_2$). Preferably, the aryl component is a $C_{6-10}$ aryl. Preferably, the alkyl component is a $C_{1-6}$ alkyl, more preferably methyl or ethyl.

In an embodiment, $R_1$ is arylalkyl. The arylalkyl group may be substituted. In an embodiment, the arylalkyl group is $C_{6-10}$ aryl-($C_{1-6}$) alkyl. In an embodiment, aryl is phenyl. In another embodiment, alkyl is $C_1$ to $C_6$ alkyl, preferably $C_1$ to $C_3$ alkyl, more preferably methyl or ethyl. Preferably, arylalkyl is benzyl or substituted benzyl (wherein the methyl component is substituted) such as 1-phenylethyl. Most preferably, arylalkyl is benzyl. Preferably, $R_2$ is benzyl. Suitably, both $R_1$ and $R_2$ are benzyl.

Preferably, Hal is bromo.

Compound (II) as shown above is depicted in the form of the (R)-enantiomer. In some embodiments, compound (II) is produced in racemic form, hereinafter termed compound (IIA), and the process further comprises resolving the racemic compound (IIA) with a resolving agent. In particular, when compound (VIII) is benzylamine, compound (II) is produced in racemic form and the process further comprises resolving the racemic compound (IIA). Suitably, the resolving agent is a chiral acid, such as L or D mandelic acid or L or D tartaric acid and the resolution produces compound (II) in the form of an acid addition salt. Optionally, the acid addition salt is converted to the free base, i.e., optically pure compound (II) after resolution. The choice of the L- or D-isomer of the chiral acid will depend on the desired enantiomer of compound (II). The skilled person would be well able to make such a choice. Preferably, compound (II) is in the form of the (R)-enantiomer and the resolving agent is L-mandelic acid. The resolution may be carried out in an alcohol solvent, such as methanol. Typically, the chiral acid salt of compound (II) is crystallized two or three times after resolution.

In other embodiments, compound (II) is produced directly from the reductive amination in optically pure form, and no further resolution is required. In particular, when compound (VIII) is (R)-1-phenylethylamine, there is no need for resolution.

Two preferred embodiments of the reductive amination are depicted in the scheme below.

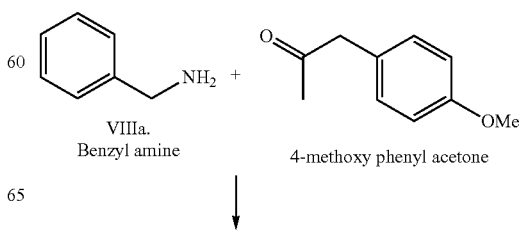

VIIIa.
Benzyl amine 4-methoxy phenyl acetone

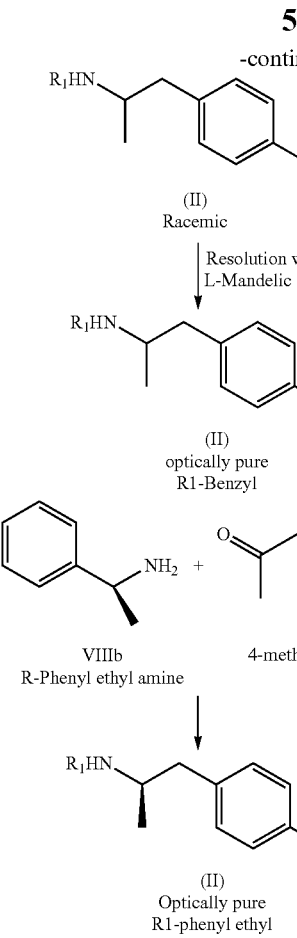

In an embodiment, the reductive amination is carried out at standard atmospheric pressure, i.e., pressure ranging from about 90 kPa to about 110 kPa, typically at a pressure of around 101 kPa.

In an embodiment, the reductive amination is carried out using an ionic compound in an organic solvent or an aqueous solvent or a mixture thereof.

The "ionic compound" is typically an inert substance. The purpose of the ionic compound is to minimize changes in the pH of a solution thereby controlling the impurity formation during the reaction and enhancing the rate of reaction. These ionic compounds not only have the potential to increase chemical reactivity and thus lead to more efficient process, but also are non-flammable and are less toxic than conventional solvents due to their low vapor pressure.

In an embodiment, the ionic compound is selected from the group consisting of ammonium acetate, ammonium chloride-ammonium hydroxide, ammonium citrate, ammonium tartrate, calcium phosphate, citrate, phosphate, potassium phosphate, potassium acetate, potassium chloride, potassium citrate, sodium acetate trihydrate, sodium chloride, triethylammonium formate, pyridinium formate, sodium perchlorate and triethylammonium formate. The ionic compounds listed may be used alone or in combination with other ionic compounds known to person skilled in the art. A preferred ionic compound is sodium acetate trihydrate.

In an embodiment, reductive amination is carried out in the presence of a solvent or solvent mixture. The solvent may be a polar solvent, for example, the polar solvent may be selected from the group consisting of methanol, ethanol, isopropyl alcohol (IPA), n-propanol, t-butanol, n-butanol, acetonitrile, tetrahydrofuran (THF), dimethylsulphoxide (DMSO), acetone, dimethylformamide (DMF), acetic acid and formic acid. In this embodiment, the reductive amination is suitably carried out at a temperature ranging from about −10° C. to about 30° C.

In an embodiment, the reductive amination is carried out at a temperature below 10° C., suitably below 5° C.

Typically, the reductive amination is carried out in the presence of a reducing agent. The reducing agent may be selected from sodium borohydride, sodium cyanoborohydride, sodium triacetoxyborohydride, potassium borohydride and potassium cyanoborohydride.

In an alternative embodiment, compound (II) may be prepared by reductive amination of 4-methoxy phenyl acetone with amine of formula (VIII); in the presence of a hydrogenating catalyst under hydrogen pressure in a solvent or mixture of solvents. In other words, the reductive amination is carried out under conditions of catalytic hydrogenation.

In an embodiment, $R_1$ is benzyl or 1-phenylethyl and the compound of formula (VIII) is designated (VIIIa) or (VIIIb) respectively.

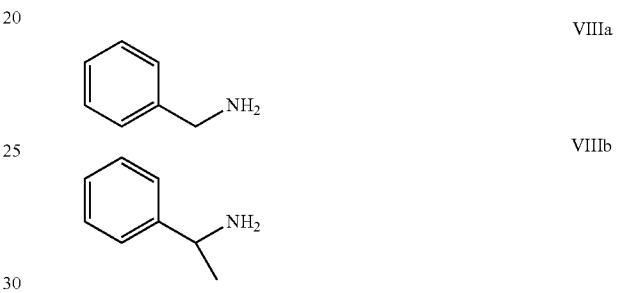

It has surprisingly been found that the use of the benzylated compound of formula (VIIIa) or (VIIIb) minimizes the formation of the dimeric impurity and regioisomer. The compound (VIIIb) may be in the form of the (R)- or the (S)-enantiomer. Preferably, compound (VIIIb) is in the form of the (R)-enantiomer.

In an embodiment, compounds (II) and (VIIIb) are optically pure.

Throughout this specification "optically pure" is to mean having an enantiomeric excess greater than 97%. Preferably, greater than 98%, most preferably greater than 99%.

Compound (II) is depicted above in the form of the (R)-isomer. The (S)-isomer may also be prepared with the reductive amination conditions being altered in order to produce the (S)-isomer, which alteration is well within the capability of the skilled person.

In an embodiment, a substantially enantiomerically pure salt of compound of formula (II) is combined with at least one equivalent of a base to produce a free base. The base is selected from organic or inorganic base, preferably sodium hydroxide.

In an embodiment, $R_1$ is substituted arylalkyl, more preferably 1-phenylethyl. When $R_1$ is 1-phenylethyl, compound (VIII) has the specific formula (VIIIb). The (R)-enantiomer of compound (II) is prepared by reacting 4-methoxyphenyl acetone with the (R)-enantiomer of 1-phenylethyl amine. Alternatively, the (S)-enantiomer of compound (II) is prepared by reacting 4-methoxyphenyl acetone with the (S)-enantiomer of 1-phenylethyl amine.

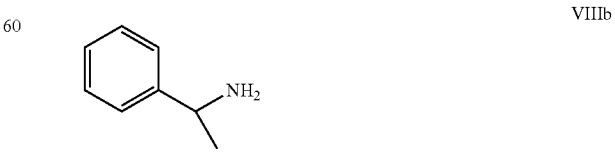

In an embodiment, there is provided a process for preparing the (R,R), (S,S), (R,S) or (S,R) diastereomer of formoterol or an acid addition salt thereof, the process comprising preparing the (R)- or (S)-enantiomer of a compound of formula (II) according to the process described above and converting the (R)- or (S)-enantiomer of the compound of formula (II) to the (R,R), (S,S), (R,S) or (S,R) diastereomer of formoterol and optionally converting the formoterol to an acid addition salt thereof. The conversion may comprise any one of the processes described below.

The present invention also provides compound (II) prepared according to any one of the processes described above.

In an embodiment, the compound of formula (II) prepared according to the process described above may be used in the process for preparing compound (IV) as described below.

According to another aspect of the present invention, there is provided a process for preparing the (R)- or (S)-enantiomer of a compound of formula (IV), which process comprises condensing the (R)- or (S)-enantiomer of an amine of formula (II) or an acid addition salt thereof with an α-haloketone of formula (III) to obtain the (R)- or (S)-enantiomer of the compound of formula (IV),

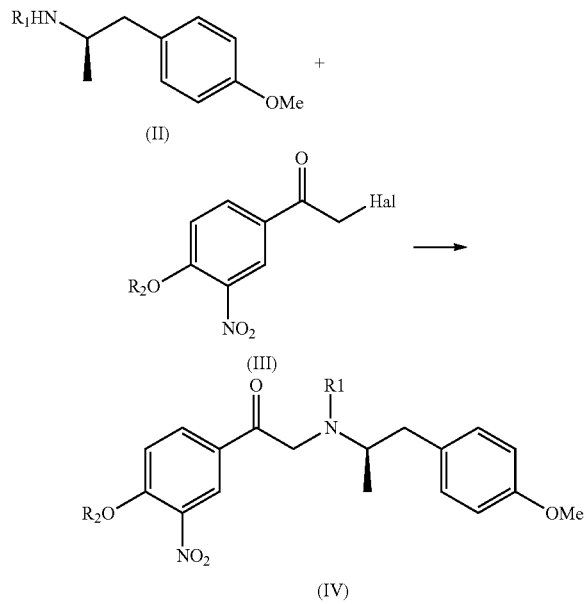

wherein $R_1$ and $R_2$ are independently optionally substituted arylalkyl, and Hal represents chloro or bromo.

In an embodiment, compound (II) is in the form of the (R)-enantiomer and compound (IV) is in the form of the (R)-enantiomer.

$R_1$ and $R_2$ function as protecting groups. If $R_1$ and/or $R_2$ are substituted arylalkyl, they may comprise one or more substituents, none of which interferes with the function of the $R_1$ and/or $R_2$ groups as protecting groups. The substituent(s) may be on the aryl component and/or on the alkyl component. In an embodiment, the substituent is on the alkyl component and is $C_{1-3}$ alkyl, preferably methyl.

$R_1$ and $R_2$ are independently an optionally substituted arylalkyl, which means that the alkyl group is covalently bonded to the aryl group and to the nitrogen of the amine moiety (in the case of $R_1$) and to the oxygen of the hydroxyl moiety (in the case of $R_2$). Preferably, the aryl component is a $C_{6-10}$ aryl. Preferably, the alkyl component is a $C_{1-6}$ alkyl, more preferably methyl or ethyl.

In an embodiment, $R_1$ is arylalkyl. The arylalkyl group may be substituted. In an embodiment, the arylalkyl group is $C_{6-10}$ aryl-($C_{1-6}$)alkyl. In an embodiment, aryl is phenyl. In another embodiment, alkyl is $C_1$ to $C_6$ alkyl, preferably $C_1$ to $C_3$ alkyl, more preferably methyl or ethyl. Preferably, arylalkyl is benzyl or substituted benzyl (wherein the methyl component is substituted) such as 1-phenylethyl. Most preferably, arylalkyl is benzyl. Preferably, $R_2$ is benzyl. Suitably, both $R_1$ and $R_2$ are benzyl.

Preferably, Hal is bromo.

In an embodiment, the condensation is carried out in the presence of a solvent. The solvent is selected from the group consisting of methanol, ethanol, isopropyl alcohol (IPA), t-butanol, methyl isobutylketone, acetone, methyl ethyl ketone, n-butanone, toluene, t-amylalcohol, acetonitrile, diglyme, tertarhydrofuran (THF), dimethylsulphoxide (DMSO), xylene and hexamethylphosphoramide (HMPA).

In an embodiment, the condensation step is carried out in the presence of an organic or inorganic base, such as triethylamine, potassium carbonate, sodium carbonate or diisopropyl ethylamine.

In an embodiment, the condensation is carried out at a temperature below 50° C., suitably below 30° C.

Optionally, a catalyst such as potassium iodide, sodium iodide, tetrabutyl ammonium bromide, 18-crown 6 ether, tetrabutyl ammonium sulphate or tetrabutyl ammonium iodide, preferably potassium iodide, may be used to enhance the rate of the reaction.

In an embodiment, there is provided a process for preparing the (R,R), (S,S), (R,S) or (S,R) diastereomer of formoterol or an acid addition salt thereof, the process comprising preparing the (R)- or (S)-enantiomer of a compound of formula (IV) according to the process described above and converting the (R)- or (S)-enantiomer of the compound of formula (IV) to the (R,R), (S,S), (R,S) or (S,R) diastereomer of formoterol and optionally converting the formoterol to an acid addition salt thereof. The conversion may comprise any one of the processes described below.

The present invention also provides compound (IV) prepared according to any one of the processes described above.

In an embodiment, the compound of formula (IV) prepared according to the process described above may be used in the process for preparing compound (V) as described below.

According to another aspect of the present invention, there is provided a process for preparing the (R,R), (S,R), (R,S) or (S,S)-diastereomer of a compound of formula (V) the process comprising chirally reducing a compound of formula (IV).

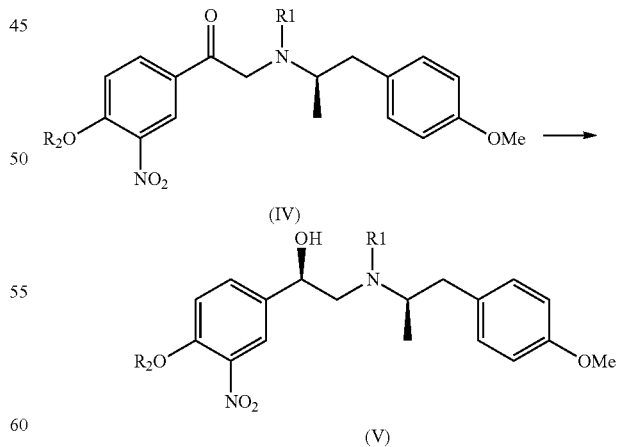

Compound (IV) has one chiral centre, but compound (V) has two chiral centres. Thus, the other chiral centre on compound (V) must be generated by selective reduction of compound (IV). In the prior art processes, there is no disclosure of the selective reduction of one out of the two chiral centres.

The process of the present invention achieves this selective reduction and is, therefore, advantageous.

In an embodiment, compound (IV) is in the form of the (R)-enantiomer and compound (V) is in the form of the (R,R)-diastereomer.

$R_1$ and $R_2$ function as protecting groups. If $R_1$ and/or $R_2$ are substituted arylalkyl, they may comprise one or more substituents, none of which interferes with the function of the $R_1$ and/or $R_2$ groups as protecting groups. The substituent(s) may be on the aryl component and/or on the alkyl component. In an embodiment, the substituent is on the alkyl component and is $C_{1-3}$ alkyl, preferably methyl.

$R_1$ and $R_2$ are independently an optionally substituted arylalkyl, which means that the alkyl group is covalently bonded to the aryl group and to the nitrogen of the amine moiety (in the case of $R_1$) and to the oxygen of the hydroxyl moiety (in the case of $R_2$). Preferably, the aryl component is a $C_{6-10}$ aryl. Preferably, the alkyl component is a $C_{1-6}$ alkyl, more preferably methyl or ethyl.

In an embodiment, $R_1$ is arylalkyl. The arylalkyl group may be substituted. In an embodiment, the arylalkyl group is $C_{6-10}$ aryl-($C_{1-6}$) alkyl. In an embodiment, aryl is phenyl. In another embodiment, alkyl is $C_1$ to $C_6$ alkyl, preferably $C_1$ to $C_3$ alkyl, more preferably methyl or ethyl. Preferably, arylalkyl is benzyl or substituted benzyl (wherein the methyl component is substituted) such as 1-phenylethyl. Most preferably, arylalkyl is benzyl. Preferably, $R_2$ is benzyl. Suitably, both $R_1$ and $R_2$ are benzyl.

In an embodiment, the compound of formula (IV) is subjected to chiral reduction using a chiral reducing agent selected from the group consisting of (−)-DIP-chloride, β-isopinocamphinyl-9BBN(R-Alpine-Borane), a chiral β-oxoaldiminatocobalt (II) complex, dioxazaluminium complex (derived from amino acid esters, $LiAlH_4$ and borane methyl sulfide), dihydrooxazaborins and a borane reducing agent in the presence of a catalytic amount of a single enantiomer of an oxazaborolidine reagent derived from a chiral oxazaborolidine catalyst.

In an embodiment, the borane reducing agent is $BH_3$, THF or borane-methyl sulfide.

In an embodiment, the chiral oxazaborolidine catalyst is selected from the group consisting of cis-(1R,2S)-aminoindanol, R-diphenyl prolinol, R-methyl oxazaborolidene (derived from R-diphenyl prolinol, trimethylboroxine and methyl boronic acid) and non-α-substituted (R)-indoline-2-carboxylic acid. The oxazaborolidine catalyst may be generated in situ from cis-(1R,2S)-aminoindanol and two equivalents of borane-methyl sulfide. Preferably, the oxazaborolidine catalyst is present in an amount ranging from about 5 to about 10% per mole of ketone (IV).

The reduction is highly enantioselective (a single isomer is typically formed with an enantiomeric excess greater than 98%, even when using a lower amount of the catalyst).

Compound (IV) as depicted above is in the form of the (R)-enantiomer. Compound (IV) for use in the process may also be in the form of the (S)-enantiomer.

Compound (V) as depicted above is in the form of the (R,R)-diastereomer. The other diastereomers of compound (V) could be prepared by reacting the appropriate enantiomer of compound (II) with the α-haloketone of formula (III) under appropriate chiral reduction conditions and following the given synthetic protocol for the (R,R)-diastereomer of the compound of formula (V). It would be well known to the skilled person which enantiomer of compound (II) and which chiral reducing agent should be used in order to prepare the different diastereomers of compound (V).

In an embodiment, the compound of formula (IV) for use in the process for preparing compound (V) is prepared according to the process described above.

The present invention also provides compound (V) prepared according to any one of the processes described above.

In an embodiment, there is provided a process for preparing the (R,R), (S,S), (R,S) or (S,R) diastereomer of formoterol or an acid addition salt thereof, the process comprising preparing the compound of formula (V) according to the process described above and converting the (R,R), (S,S), (R,S) or (S,R) diastereomer of a compound of formula (V) to the (R,R), (S,S), (R,S) or (S,R) diastereomer of formoterol, and optionally converting the formoterol to an acid addition salt thereof. The conversion may involve any one of the processes described below.

According to another aspect of the present invention, there is provided a process for preparing the (R,R), (S,S), (R,S) or (S,R) diastereomer of a compound of formula (VI), the process comprising reducing the (R,R), (S,S), (R,S) or (S,R) diastereomer of compound (V) to produce the (R,R), (S,S), (R,S) or (S,R) diastereomer of the compound of formula (VI);

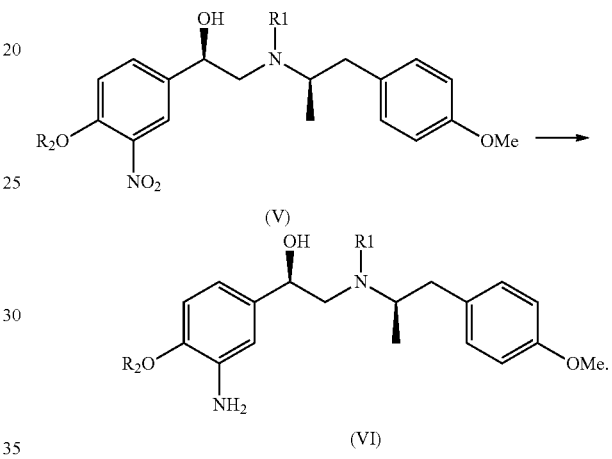

The process of the present invention is advantageous as the configuration of compound (V) is retained.

In an embodiment, the (R,R) diastereomer of the compound of formula (V) is reduced to obtain the (R,R) diastereomer of a compound of formula (VI).

$R_1$ and $R_2$ function as protecting groups. If $R_1$ and/or $R_2$ are substituted arylalkyl, they may comprise one or more substituents, none of which interferes with the function of the $R_1$ and/or $R_2$ groups as protecting groups. The substituent(s) may be on the aryl component and/or on the alkyl component. In an embodiment, the substituent is on the alkyl component and is $C_{1-3}$ alkyl, preferably methyl.

$R_1$ and $R_2$ are independently an optionally substituted arylalkyl, which means that the alkyl group is covalently bonded to the aryl group and to the nitrogen of the amine moiety (in the case of $R_1$) and to the oxygen of the hydroxyl moiety (in the case of $R_2$). Preferably, the aryl component is a $C_{6-10}$ aryl. Preferably, the alkyl component is a $C_{1-6}$ alkyl, more preferably methyl or ethyl.

In an embodiment, $R_1$ is arylalkyl. The arylalkyl group may be substituted. In an embodiment, the arylalkyl group is $C_{6-10}$ aryl-($C_{1-6}$) alkyl. In an embodiment, aryl is phenyl. In another embodiment, alkyl is $C_1$ to $C_6$ alkyl, preferably $C_1$ to $C_3$ alkyl, more preferably methyl or ethyl. Preferably, arylalkyl is benzyl or substituted benzyl (wherein the methyl component is substituted) such as 1-phenylethyl. Most preferably, arylalkyl is benzyl. Preferably, $R_2$ is benzyl. Suitably, both $R_1$ and $R_2$ are benzyl.

The reduction is a reduction of the nitro group. The reduction is enantiomerically selective. In an embodiment, the nitro reduction is carried out using a hydrogen donating compound in the presence of a hydrogen transfer catalyst with retention of configuration.

Suitably, the hydrogen donating compound is hydrazine hydrate.

Suitably, the hydrogen transfer catalyst is selected from the group consisting of FeCl$_3$.6H$_2$O-activated carbon, Fe (III) oxide hydroxide, Fe (III) oxide, Zn—C, Fe—C, Pd—C, Pt—C, Raney Ni, graphite and clays.

In an embodiment, the nitro compound is reduced with hydrazine hydrate, supported on a solid material such as alumina, silica gel and clay. This process provides a reduced reaction time, easier work-up procedure and enhanced selectivity and reactivity without racemization.

In an embodiment, the reduction is conducted in refluxing alcoholic solvents or dioxane.

In an alternative embodiment, the nitro group is reduced to the amine group by ammonium formate using a hydrogenation catalyst in the presence of an inert solvent. Suitably, the inert solvent is selected from an alcohol solvent such as methanol, ethanol, isopropyl alcohol or butanol, or a polar aprotic solvent such as acetonitrile, DMF (Dimethylformamide), DMSO or THF.

In yet another alternative embodiment, the nitro group is reduced to the amine group by heterogeneous catalytic hydrogenation in the presence of a noble metal catalyst such as PtO$_2$ or Pt/C. Suitably, the hydrogenation catalyst includes noble metal catalysts such as palladium, ruthenium or rhodium supported on carbon, clay, silica or alumina. In this embodiment, the reduction is suitably carried out at a temperature ranging from about 25° C. to about reflux temperature of the solvent used.

In an embodiment, the compound of formula (V) for use in the process for preparing compound (VI) is prepared according to the process described above.

The present invention also provides compound (VI) prepared according to any one of the processes described above.

In an embodiment, there is provided a process for preparing the (R,R), (S,S), (R,S) or (S,R) diastereomer of formoterol or an acid addition salt thereof, the process comprising preparing the compound of formula (VI) according to the process described above and converting the (R,R), (S,S), (R,S) or (S,R) diastereomer of a compound of formula (VI) to the (R,R), (S,S), (R,S) or (S,R) diastereomer of formoterol, and optionally converting the formoterol to an acid addition salt thereof. The conversion may involve any one of the processes described below.

In an embodiment, the conversion of compound (VI) comprises formylating the (R,R), (S,S), (R,S) or (S,R) diastereomer of compound (VI) to produce the (R,R), (S,S), (R,S) or (S,R) diastereomer of compound (VII);

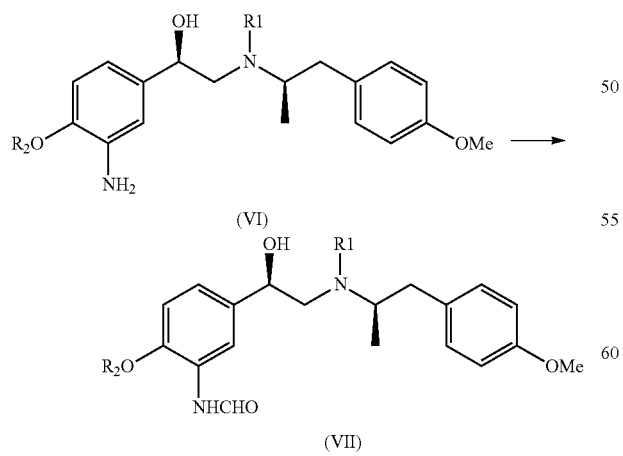

optionally, reacting the (R,R), (S,S), (R,S) or (S,R) diastereomer of compound (VII) with an acid to form the (R,R), (S,S), (R,S) or (S,R) diastereomer of a compound of formula (VIIa) and optionally isolating the (R,R), (S,S), (R,S) or (S,R) diastereomer of compound (VIIa);

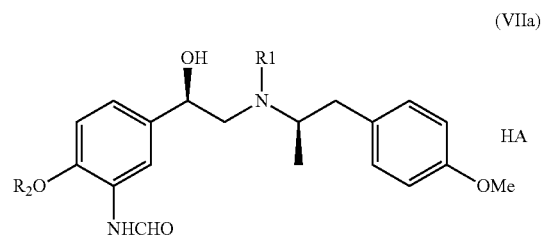

wherein R$_1$ and R$_2$ are as defined above and HA is an acid of formula H$^+$A$^-$, wherein A$^-$ is an anion; and deprotecting the (R,R), (S,S), (R,S) or (S,R) diastereomer of compound (VII) or the (R,R), (S,S), (R,S) or (S,R) diastereomer of compound (VIIa) to obtain the (R,R), (S,S), (R,S) or (S,R) diastereomer of formoterol.

Compound (I) is depicted above in the form of the (R,R)-diastereomer. The other diastereomers of compound (I) could be prepared using the appropriate diastereomer of compound (V) as a starting material.

In the compound (VIIa), the anion A$^-$ corresponds to the acid used to form the acid addition salt. Optionally, the acid is a carboxylic acid, such as benzoic acid, oxalic acid, maleic acid, succinic acid, fumaric acid or tartaric acid; or a mineral acid, such as hydrochloric acid.

In an embodiment, the (R,R) diastereomer of the compound of formula (VII) is isolated, in the form of its acid addition salt as the (R,R) diastereomer of a compound of formula (VIIa).

In an embodiment, the (R,R) diastereomer of the compound of formula (VII) or (VIIa) is converted to the corresponding (R,R) diastereomer of formoterol. Suitably, the conversion comprises deprotection of the NR$_1$ and OR$_2$ groups using a suitable deprotecting reagent. As is well known to the skilled person, the deprotection reagent depends on the nature of the protecting group.

When R$_1$ and R$_2$ are benzylic group, the deprotection may comprise hydrogenolysis of the compound of formula (VII) or (VIIa) in the presence of a noble metal catalyst and hydrogen gas.

The present invention also provides the (R,R), (S,S), (R,S) or (S,R) diastereomer of formoterol or an acid addition salt thereof prepared according to any one of the processes described above.

The formoterol or enantiomers and acid addition salts thereof so prepared may be formulated with one or more pharmaceutically acceptable excipients to provide a pharmaceutical composition. Such excipients and compositions are well known to those skilled in the art.

DETAILED DESCRIPTION OF THE INVENTION

In a preferred embodiment of the present invention, there is provided an improved synthesis of the (R,R), (S,S), (R,S) or (S,R) diastereomer of formoterol or an acid addition salt thereof, as depicted below in reaction scheme 1.

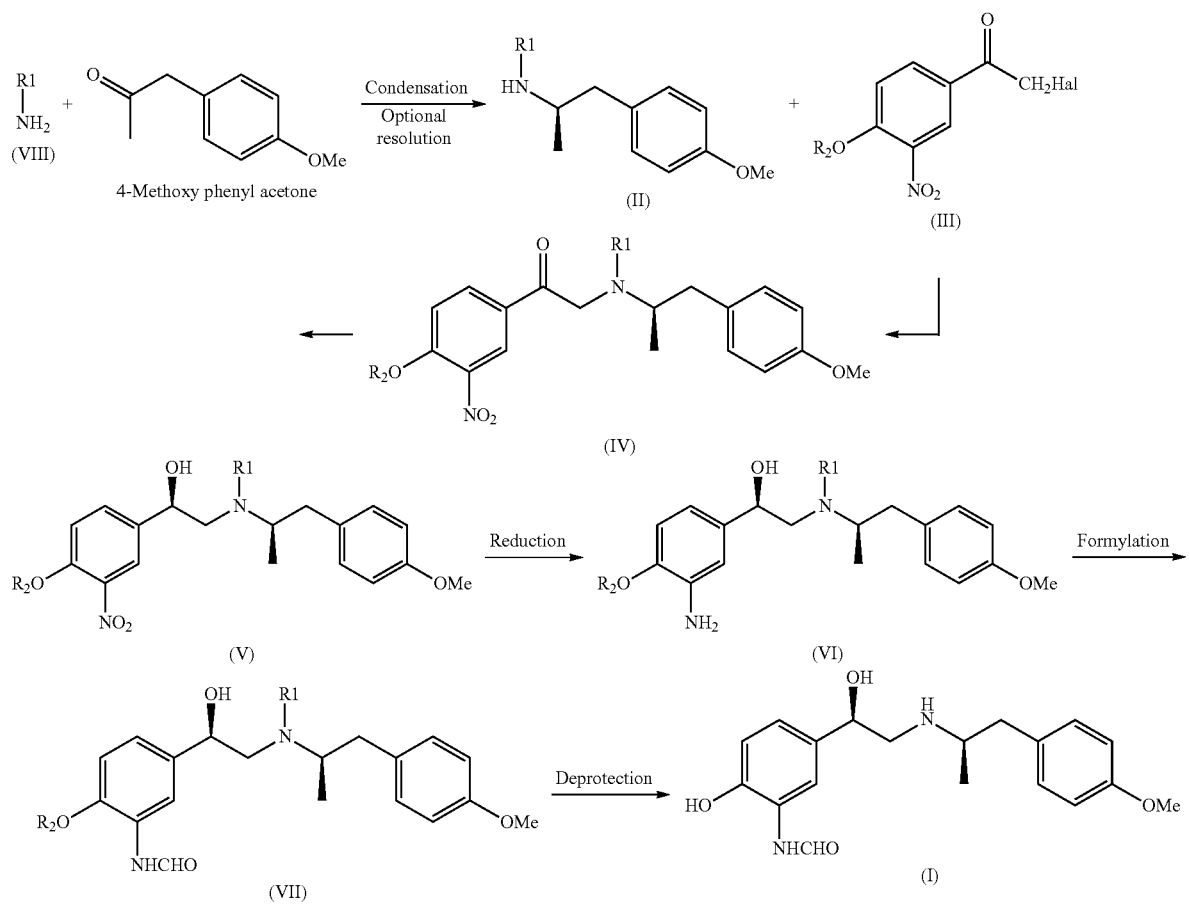

Compounds (I), (V), (VI) and (VII) are depicted above in the form of the (R,R)-diastereomer. Compounds (II) and (IV) are depicted above in the form of the (R)-enantiomer. It is to be understood that the present invention also relates to processes for preparing the (S,S), (R,S) and (S,R) diastereomers of compounds (I), (V), (VI) and (VII), and to processes for preparing the (S)-isomer of compounds (II) and (IV).

Accordingly, in a preferred embodiment, the present invention provides a process for the preparation of (R,R)-formoterol (also known as arformoterol) of formula (I) or an acid addition salt thereof, comprising the following steps.

Reductive amination of 4-methoxyphenyl acetone with an amine of formula (VIII),

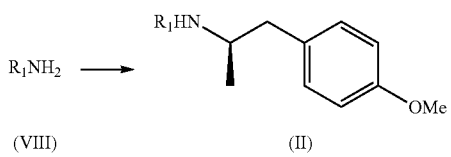

wherein $R_1$ is as defined above in the presence of a suitable reducing agent to obtain a compound of formula (II) or an acid addition salt thereof.

In an embodiment, $R_1$ is benzyl, and compound (VIII) has the formula (VIIIa). In another embodiment, $R_1$ is 1-phenylethyl and compound (VIII) has the formula (VIIIb).

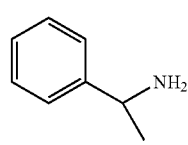

When compound (VIIIa) is subjected to reductive amination with 4-methoxyphenyl acetone, compound (II) is produced in racemic form and the process further comprises resolving racemic compound (II) with a reducing agent and producing optically pure compound (II). Preferably, the resolving agent is a chiral acid and the reaction of the racemic compound (II) with the acid produces a resolved salt of compound (II) which is then converted to optically pure compound (II), for example, by reaction with a base. Preferably, the (R)-enantiomer of compound (II) in which $R_1$ is benzyl is prepared by reductive amination with 4-methoxyphenyl acetone, reaction of the racemic compound (II) with L-mandelic acid in an alcohol solvent, such as methanol, to obtain the L-mandelate salt of the (R)-enantiomer of compound (II), and conversion of the salt to the free base form of the (R)-enantiomer of compound (II).

When compound (VIIIb) is subjected to reductive amination with 4-methoxyphenyl acetone, compound (II) is produced in optically pure form, so no resolution step is required.

Preferably, the reductive amination is carried out at standard atmospheric pressure using an ionic compound in an organic solvent or an aqueous solvent or mixture thereof.

Alternatively, reductive amination may be carried out under catalytic hydrogenation in the presence of a suitable hydrogenating catalyst and a suitable solvent. The step of preparing compound (II) from compound (VIII) and 4-methoxyphenyl acetone forms another aspect of the present invention.

The (R)-enantiomer of compound (II) or an acid addition salt thereof is condensed with an α-haloketone of formula (III)

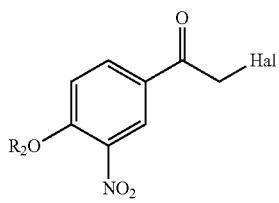

(III)

to obtain a compound of formula (IV);

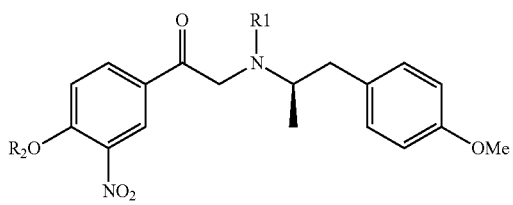

(IV)

wherein $R_1$ and $R_2$ are as defined above; and the (R)-enantiomer of compound (IV) is chirally reduced to form the (R,R)-diastereomer of a compound of formula (V);

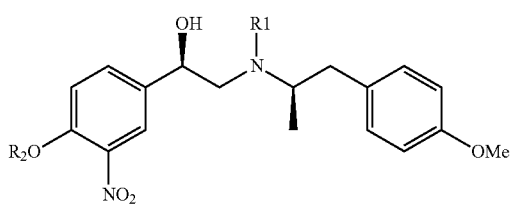

(V)

wherein $R_1$ and $R_2$ are as defined above.

The (R,R)-diastereomer of compound V is reduced to form the corresponding (R,R)-diastereomer of formula (VI) using a hydrogen donating compound.

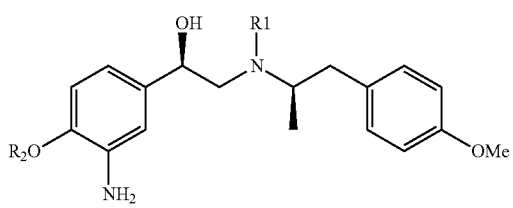

(VI)

The (R,R)-diastereomer of compound (VI) is formylated in the presence of a suitable formylating agent to obtain the corresponding (R,R)-diastereomer of compound (VII)

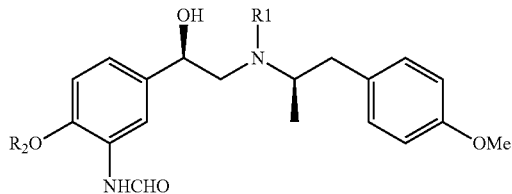

(VII)

wherein $R_1$ and $R_2$ are as defined above.

Optionally, the (R,R)-diastereomer of compound (VII) is converted to a salt thereof of formula (VIIa)

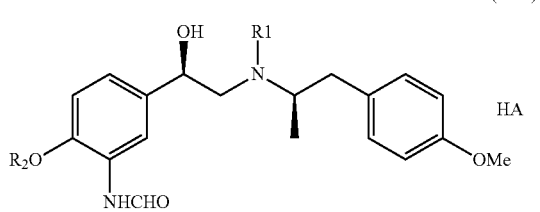

(VIIa)

wherein $R_1$, $R_2$ and HA are as defined above.

The (R,R)-diastereomer of compound (VII) is deprotected under suitable deprotecting conditions to obtain the corresponding (R,R)-diastereomer of formoterol (arformoterol) of formula (I).

Optionally, arformoterol of formula (I) is converted to a pharmaceutically acceptable salt thereof.

Typically, the reductive amination is carried out in a solvent such as methanol, ethanol, IPA, n-propanol, t-butanol, n-butanol, acetonitrile, THF, DMSO, acetone, DMF, acetic acid, formic acid or a mixture thereof. The reaction is preferably carried out at a temperature ranging from about −10° C. to about 30° C., preferably from about 0-5° C. The suitable reducing agent used may be selected from sodium borohydride, sodium cyanoborohydride, sodium triacetoxyborohydride, potassium borohydride and potassium cyanoborohydride.

The ionic compounds may be selected from the group consisting of ammonium acetate, ammonium chloride-ammonium hydroxide, ammonium citrate, ammonium tartrate, calcium phosphate, citrate, phosphate, potassium phosphate, potassium acetate, potassium chloride, potassium citrate, sodium acetate trihydrate, sodium chloride, triethylammonium formate, pyridinium formate, sodium perchlorate and triethylammonium formate. The ionic compound may be used alone or in combination with other ionic compounds known to person skilled in the art. A preferred ionic compound is sodium acetate trihydrate. Sodium acetate trihydrate is added to maintain the pH of the reaction mixture thereby making reaction faster and reduces formation of impurities.

More particularly, the compound of formula (VIII) wherein $R_1$ is benzyl or 1-phenylethyl, may be subjected to reductive amination with 4-methoxyphenyl acetone to give the corresponding compound of formula (II).

In an alternative embodiment, reductive amination is carried out with hydrogen in the presence of hydrogenation catalyst. A typical hydrogenation catalyst may be selected from Raney Nickel, palladium, palladium hydroxide, palladium on activated carbon palladium on alumina, platinum, platinum on activated carbon and Rh(I) and Ru(II) triphenylphosphine complexes. The solvent used may be selected from methanol, ethanol, isopropyl alcohol, THF, toluene and mixtures thereof. The reaction may be carried out at a temperature ranging from about 25° C. to about 70° C., preferably from about 40 to about 60° C., more preferably from about 50 to about 55° C.

When $R_1$ is benzyl, the compound of formula (II) may be further resolved using a suitable resolving agent such as mandelic acid, to obtain the (R)-enantiomer of compound (II). The reaction may be carried out in an alcoholic solvent such as methanol at a suitable temperature.

Compound (II) may be isolated in the form of its acid addition salt such as hydrochloride, mandelate, fumarate, tartrate.

Typically, optically pure compound (II) as a free base or acid addition salt thereof, preferably base is condensed with the compound of formula (III) in a solvent such as methanol, ethanol, IPA, t-butanol, acetone, methyl isobutylketone, 2-butanone, ethyl acetate, toluene, t-amylalcohol, acetonitrile, diglyme, DMSO, xylene, or hexamethyl phosporamide (HMPA) or THF. The reaction may be carried out at a temperature of from cooling to reflux temperature of solvent, preferably under cooling. Further, this reaction may be carried out optionally in the presence of, either organic or inorganic base, such as triethylamine, potassium carbonate, sodium carbonate or diisopropylethylamine to accelerate the reaction. In an embodiment, an inorganic base is used. Optionally, a catalyst such as potassium iodide, sodium iodide, tetrabutyl ammonium bromide, 18-crown-6, tetrabutyl ammonium sulphate or tetrabutyl ammonium iodide, preferably potassium iodide, may be used to enhance the rate of the reaction.

More particularly, the optically pure compound of formula (II) wherein $R_1$ is benzyl or 1-phenylethyl, may be condensed with the compound (III), wherein $R_2$ is benzyl and Hal is bromo, at about 20-30° C., to give the corresponding compound of formula (IV). Use of the benzylated compound of formula (II) minimizes the formation of the dimeric impurity; this forms a preferred embodiment of the present invention.

The compound (III) can be obtained by any process known in the art, for example, U.S. Pat. No. 3,994,974.

Further, the compound (IV) is subjected to chiral reduction using chiral reducing agents such as (−)-DIP chloride, β-isopinocamphinyl-9BBN (R-Alpine-Borane). The reduction may be carried out in the presence of about one equivalent of a borane reducing agent such as $BH_3$, THF or borane-methyl sulfide, and optionally in the presence of a catalytic amount of a single enantiomer of an oxazaborolidine derived from chiral oxazaborolidine catalyst, to obtain a compound of formula (V).

Examples of chiral oxazaborolidine catalysts are cis-(1R, 2S)-aminoindanol, R-diphenyl prolinol, R-methyl oxazaborolidene (derived from R-diphenyl prolinol, trimethylboroxine and methyl boronic acid), non-α-substituted (R)-indoline-2-carboxylic acid, etc.

The compound (V) may be reduced to corresponding amine of formula (VI) by using a hydrogen donating compound preferably hydrazine hydrate in the presence of hydrogen transfer catalysts. Suitable hydrogen transfer catalysts are $FeCl_3.6H_2O$-activated carbon, Fe (III) oxide hydroxide or Fe (III) oxide, Zn—C, Fe—C, Pd—C, Pt—C, Raney Ni, graphite and clays. The nitro compound is reduced with hydrazine hydrate supported on solid materials such as alumina, silica gel and clay, which provides reduced reaction time, easier work-up procedure and enhanced selectivity and reactivity without racemization. Solvents used for the process are selected from alcoholic solvents or dioxane.

Alternatively, the nitro compounds can be reduced to amines with the retention of stereoconfiguration by the use of ammonium formate as a hydrogen transfer reagent using a hydrogenation catalyst in the presence of an inert solvent. Suitable inert solvent employed, may be selected from alcohol solvents such as methanol, ethanol, isopropyl alcohol, butanol or polar aprotic solvents such as acetonitrile, DMF, DMSO, THF. Suitably, the hydrogenation catalyst includes noble metal catalysts such as palladium, platinum, ruthenium or rhodium supported on carbon, clay, silica or alumina. The reduction is suitably carried out at a temperature ranging from about 25° C. to about reflux temperature of the solvent used.

Alternatively, the nitro group may be selectively reduced to the amine group by heterogeneous catalytic hydrogenation in the presence of a noble metal catalyst such as $PtO_2$ or Pt/C in the presence of suitable solvent such as THF, toluene, alcoholic solvents or mixture thereof. The reduction is carried out at a temperature below 60° C.; preferably below 40° C., most preferably below 30° C.

Aniline of formula (VI) is formylated with formic acid or formic acid/acetic anhydride without racemization. In the process of present invention, mixture of formic acid and acetic anhydride is used. The formylation may be performed in the presence of inert organic solvent or solvent mixture selected from halogenated hydrocarbons such as methylene chloride, chloroform and ethylene chloride, aromatic hydrocarbons such as toluene and xylene, ethers, ethyl acetate or in the absence of the solvent. The reaction is preferably carried out in a mixture of toluene-THF at a temperature of from cooling to heating, preferably at 20-30° C.

The compound (VII) may be isolated in the form of its acid addition salt as a compound of formula (VIIa).

Typically, where $R_1$ is benzyl or substituted benzyl, a preferred method for deprotection of formula (VII) to arformoterol of formula (I), is catalytic reduction using catalysts such as palladium, palladium hydroxide, palladium on activated carbon, palladium on alumina, platinum, platinum on activated carbon and Raney nickel. The solvent used may be selected from alkyl acetate, lower alkylamines, alcohols, aliphatic hydrocarbons, aromatic hydrocarbons, heterocycles, dialkylethers, an acid, mixture of water and water miscible solvents, ionic liquids, halogenated solvents and mixtures thereof.

The process of the present invention may further comprise: converting arformoterol of formula (I) to a pharmaceutically acceptable salt thereof. The acid addition salts include inorganic acids such as hydrochloric acid, hydrobromic acid, sulfuric acid, nitric acid, phosphoric acid, pivalic acid and organic salts such as fumaric acid, tartaric acid, acetic acid, oxalic acid, malonic acid, mandelic acid, succinic acid, maleic acid, lactic acid, citric acid, methane sulfonic acid, p-hydroxy benzoic acid, glutmic acid, p-toluene sulfonic acid, preferably fumaric acid and tartaric acid.

The arformoterol obtained by the process of present invention is free of other diastereomers.

The other diastereomers of formoterol may be prepared by reacting the appropriate enantiomer following the synthetic protocol given above for arformoterol.

According to another aspect of the present invention, there is provided a pharmaceutical composition comprising arformoterol or acid addition salts thereof as described above together with one or more pharmaceutically acceptable excipients.

According to yet another aspect of the present invention, there is provided the use of arformoterol or acid addition salts thereof as described above in medicine.

According to a still further aspect of the present invention, there is provided the use of arformoterol or acid addition salts thereof as described above in the treatment of asthma or COPD (Chronic Obstructive Pulmonary Disease).

According to a still further aspect of the present invention, there is provided the use of arformoterol or acid addition salts thereof as described above in the manufacture of a medicament for the treatment of asthma or COPD.

According to another aspect of the present invention, there is provided a method of treating asthma and COPD, comprising administering to a patient in need thereof arformoterol or acid addition salts thereof as described above.

EXAMPLES

The invention will now be illustrated further by the following non-limiting Examples.

Example 1

Step 1. Preparation of (R)—N-benzyl-N-(1-methyl-2-p-methoxyphenylethyl)amine hydrochloride
Preparation-1

4-Methoxy phenyl acetone (50 kg, 0.305 M), sodium acetate trihydrate (62 kg, 0.455 M) were charged in to the reactor containing acetic acid (170 kg,) and methanol (160 lit). The reaction mass was chilled to 0-5° C. Benzylamine (36 kg, 0.336 M) was added slowly into the reactor maintaining temperature between 0-5° C. After stirring for two hours at 0-5° C., the reaction mass was treated with sodium borohydride (25 kg, 0.657 M) maintaining temperature below 10° C. and was stirred further for 2 hours. The reaction mass was diluted with water (500 lit) and treated with a solution of sodium hydroxide (70 kg sodium hydroxide in 150 lit water) below 30° C. The reaction mass was extracted with methylene chloride twice (200 lit), washed with water and concentrated under reduced pressure. The residue obtained was dissolved in ethyl acetate (200 lit), cooled to 10-15° C. and the pH of reaction mass was adjusted to 1-2 with IPA+HCl. The solids were isolated by filtration, dried to yield title compound as hydrochloride salt. (50 Kg, 56.5%)

Preparation-2

4-Methoxy phenyl acetone (200 gms, 1.219 moles), benzylamine (124 gms, 1.158 moles), Raney-Nickel (30 gms) and methanol (1.4 lits) were introduced in an autoclave. Hydrogenated the reaction mass by applying 10 kg hydrogen pressure at 65-70° C. for 6-8 hrs. The reaction mass was cooled to 25-30° C. The catalyst was removed by filtration and the clear filtrate was acidified with IPA-HCl. The reaction mass was concentrated under reduced pressure below 50° C. Charged ethyl acetate (1.2 lits) and continued distillation to obtain residue. The residue was stirred with ethyl acetate (0.4 lit) for 30 mins at 50° C. and then for 2 hours at 25-30° C. The solids were isolated by filtration, washed with ethyl acetate (0.2 lit) and dried to yield title compound as hydrochloride salt. (220 gms, 62%)

Step 2. Preparation of (R)—N-benzyl-N-(1-methyl-2-p-methoxyphenylethyl)amine mandalate The hydrochloride salt (50 kg) was treated with 20% aqueous sodium hydroxide solution. The reaction mass was extracted with dichloromethane, washed with water and organic extract evaporated. The residue obtained was dissolved in methanol (500 lits). L-mandelic acid (26.16 kg, 0.172 M) was charged and the reaction mixture heated to reflux for 1 hour. The solution was cooled to 25-30° C., stirred for 18-20 hours and the mandelate salt filtered off. Three recrystallizations from methanol provided 13.5 kg of title compound having enantiomeric purity of 99.9%.

Example 2

Preparation of (R)—N-Phenylethyl-N-(1-methyl-2-p-methoxyphenylethyl)amine hydrochloride The title compound was prepared from R-(+)-phenyl ethylamine (500 gms, 4.132 M) using a similar method to that described in example 1, preparation 1.
Yield: ~500 gms (45.16%)

Example 3

(R)—N-benzyl-N-(1-methyl-2-p-methoxyphenylethyl) amine mandalate (13.5 kg, 0.033 M) was stirred in 67.5-lit water. The reaction mass was then basified to pH 9-10 with 20% aqueous sodium hydroxide solution and extracted in dichloromethane (67.5 lits). The organic extract was separated, washed with water, dried on sodium sulphate and evaporated.

Preparation of 4-benzyloxy-3-nitro-α-[N-benzyl-N-(1-methyl-2-p-methoxyphenyl ethyl)amino]acetophenone 4-Benzyloxy-3-nitro-α-bromoacetophenone (12.5 kg, 0.0358 M), potassium carbonate (7.0 kg, 0.050 M), potassium iodide (0.75 kg) in acetone (125 lits) and (R)—N-benzyl-N-(1-methyl-2-p-methoxy phenyl ethyl) amine (8.5 kg, 0.0334 M) were stirred for 3 hours at 25-30° C. The insoluble was removed by filtration. The clear filtrate was evaporated and the residue was partitioned between dichloromethane (7.5 lits) and water (7.50 lits). The organic extract was separated, washed with water and evaporated to obtain the title compound.

Example 4

Preparation of 4-benzyloxy-3-nitro-α-[N-benzyl-N-(1-methyl-2-p-methoxyphenyl ethyl)aminomethyl] benzyl alcohol Tetrahydrofuran (500 ml) and R-methyloxazaborolidine (42 ml) were charged in a reactor. The reaction mass was cooled to −10° C. Borane-dimethyl sulfide complex (110 ml) was added slowly. A solution of 4-Benzyloxy-3-nitro-α-[N-benzyl-N-(1-methyl-2-p-methoxy phenyl ethyl)amino]acetophenone (100 gms, 0.19 M) in 500 ml THF was added slowly to the reaction mass at −10 to −5° C. The reaction mass was further stirred for 1.5 hours and treated with 2% aqueous HCl (500 ml). The reaction mass was extracted with 1.0 liter toluene, washed with water and clear filtrate concentrated under reduced pressure below 40° C. to yield the title compound. (95 gms)

Example 5

Preparation of 3-amino-4-benzyloxy-α-[N-benzyl-N-(1-methyl-2-p-methoxyphenyl ethyl)aminomethyl]benzyl alcohol i) Using Hydrazine Hydrate (Standard Atmospheric Pressure)
4-Benzyloxy-3-nitro-α-[N-benzyl-N-(1-methyl-2-p-methoxyphenylethyl)aminomethyl]benzyl alcohol (100 gms, 0.19 M), hydrazine hydrate (50 gms, 1.56 M), neutral alumina (20 gms), charcoal (10 gms), water (50 ml) and methanol (500 ml) were mixed together. The reaction mass was heated to 50° C. A solution of ferric chloride (2 gms, 0.012 M) in 50 ml methanol was introduced slowly at 55-60° C. The reaction mass was filtered over hyflo and the clear filtrate evaporated. The residue obtained was dissolved in 1.0-lit toluene, washed organic extract with water, evaporated to obtain title compound. (75 gms, 79%)

ii) Using 5% Pt/C (Catalytic Hydrogenation).

4-benzyloxy-3-nitro-α-[N-benzyl-N-(1-methyl-2-p-methoxyphenylethyl)aminomethyl]benzyl alcohol (165 gms, 0.313 M), 5% Platinum on carbon (16.5 gms) and THF (0.66 lit) were mixed in a hydrogenator. The reaction mass was hydrogenated at 25-30° C. by applying 2 kg pressure for 7-10 hrs. The catalyst was removed by filtration and the clear filtrate evaporated. The residue was dissolved in toluene (0.825 lit) and evaporated to yield the title compound. (125 gms, 80%)

iii) Using Ammonium Formate a) in DMF

To a solution of 4-benzyloxy-3-nitro-α-[N-benzyl-N-(1-methyl-2-p-methoxyphenylethyl)aminomethyl]benzyl alcohol (100 gms, 0.19 M) in DMF (500 ml) was added 10% Pd/C. The resulting mass was heated to 40° C. and ammonium formate (36 gms, 0.57 M) was added in lots in 1 hour. The reaction mass was heated slowly to 70-75° C. for 1 hour, then cooled to 50° C. The catalyst was removed by filtration and the clear filtrate evaporated. The residue was stirred in water (500 ml) and basified with liq. Ammonia. The reaction mass was extracted in 1.0-lit toluene, washed organic extract with water, dried on sodium sulfate and evaporated to obtain title compound. (80 gms, 84.21%)

b) in SPDS (Specially Denatured Alcohol)

To a solution of 4-benzyloxy-3-nitro-α-[N-benzyl-N-(1-methyl-2-p-methoxyphenylethyl)aminomethyl]benzyl alcohol (100 gms, 0.19 M) in SPDS (1.0 lit) was added 10% Pd/C. The resulting mass was heated to 40° C. and ammonium formate (36 gms, 0.57 M) was added in lots in 1 hour. The reaction mass was heated slowly to 70° C. for 1 hour, and then cooled to 50° C. The catalyst was removed by filtration and the clear filtrate evaporated. The residue was stirred in water (500 ml) and basified with liq. Ammonia. The reaction mass was extracted in 1.0-lit toluene, washed organic extract with water, dried on sodium sulfate and evaporated to obtain title compound. (78 gms, 83%)

Example 6

Preparation of 4-benzyloxy-3-formylamino-α-[N-benzyl-N-(1-methyl-2-p-methoxy phenylethyl)aminomethyl]benzyl alcohol 3-amino-4-benzyloxy-α-[N-benzyl-N-(1-methyl-2-p-methoxyphenylethyl)aminomethyl]benzyl alcohol (100 gms, 0.2 M), toluene 0.2 lit and 0.2 lit THF, were charged in a reactor. The reaction mass was cooled to 15° C. and 35 ml of 3:2 formic acid-acetic anhydride was introduced maintaining temperature below 20° C. The reaction mass was further stirred at 20-30° C. for 1 hour and concentrated under reduced pressure. The residue obtained was dissolved in toluene (0.65 lit) and basified with liquor ammonia. The organic layer was separated, washed with water and concentrated under reduced pressure below 35° C. to yield the title compound. (100 gms, 94.66%)

Example 7

Preparation of Arformoterol 4-benzyloxy-3-formylamino-α-[N-benzyl-N-(1-methyl-2-p-methoxyphenylethyl)aminomethyl]benzyl alcohol (120 gms, 0.23 M), 10% Pd/C (12 gms) and denatured spirit (0.6 lit) were introduced in an autoclave. The reaction mass was hydrogenated by applying 4 kg hydrogen pressure at 25-30° C. for 3 hrs. The catalyst was removed by filtration and the clear filtrate concentrated under reduced pressure below 40° C. to yield the title compound. (63 gms, 80%).

Example 8

Preparation of Arformoterol Tartrate

Arformoterol base (60 gms, 0.17 M), 480 ml IPA, 120 ml toluene and a solution of L(+)-tartaric acid (25.6 gms, 0.17 M) in 60 ml distilled water were stirred at 25-30° C. for 2 hrs and further at 40°-45° C. for 3 hrs. The reaction mass was cooled to 25-30° C. and further chill to 20° C. for 30 mins. The solid obtained was isolated by filtration to yield the title compound. (60 gms, 70%)

The tartrate salt was dissolved in hot 50% IPA-water (0.3 lit), cooled as before and filtered to provide arformoterol tartrate (30 gms, 50% w/w) having enantiomeric purity greater than 99%.

It will be appreciated that the invention may be modified within the scope of the appended claims.

The invention claimed is:

1. A process for preparing a compound of formula (VI) or a salt thereof

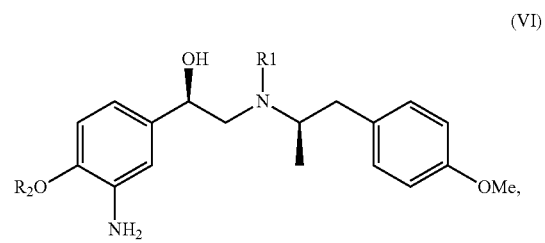

the process comprising:

(i) reacting 4-methoxyphenyl acetone with an amine of formula (VIII) under conditions of reductive amination to produce a compound of formula (II) or a salt thereof, wherein there is no isolation of an imine intermediate formed during the reductive amination and wherein the reductive amination is carried out in the presence of an ionic compound and a reducing agent, wherein the ionic compound is sodium acetate trihydrate and the reducing agent is sodium borohydride,

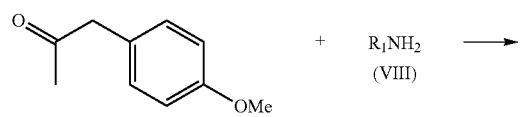

-continued

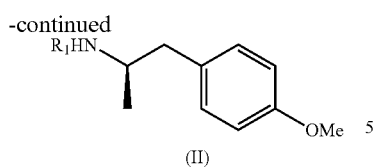

(II)

(ii) condensing the compound of formula (II) or an acid addition salt thereof with an α-haloketone of formula (III) to produce a compound of formula (IV)

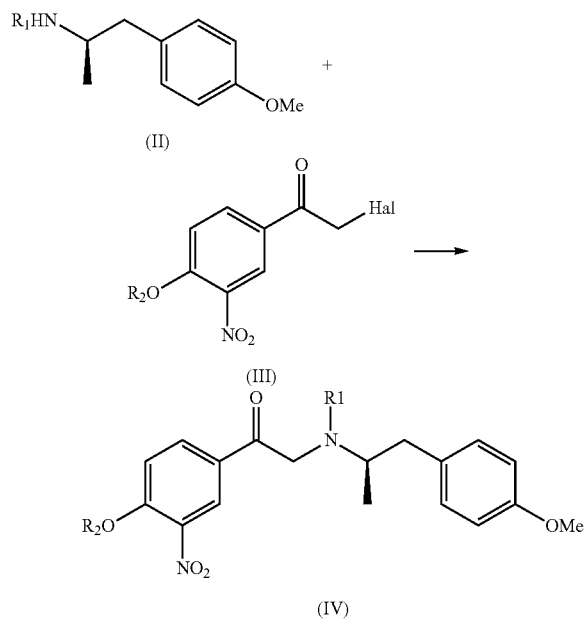

(iii) reducing the compound of formula (IV) to a compound of formula (V),

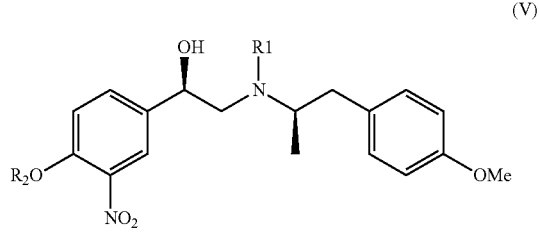

wherein the compound of formula (IV) in step (iii) is subjected to chiral reduction using a chiral reducing agent selected from the group consisting of (−)-DIP-chloride, β-isopinocamphinyl-9BBN (R-Alpine-Borane); a chiral β-oxoaldiminatocobalt (II) complex, a dioxazaluminium complex derived from amino acid esters, LiAlH4 and borane methyl sulfide, and dihydrooxazaborins; in the presence of a catalytic amount of a single enantiomer of an oxazaborolidine reagent derived from a chiral oxazaborolidine catalyst, and (iv) reducing the compound of formula (V) to the compound of formula (VI), wherein the reduction of step (iv) is carried out by either (1) a hydrogen donating compound in the presence of a hydrogen transfer catalyst or (2) ammonium formate using a hydrogenation catalyst, wherein $R_1$ and $R_2$ are independently optionally substituted arylalkyl, and Hal is selected from chloro or bromo.

2. The process according to claim 1, wherein $R_2$ is benzyl.

3. The process according to claim 1, wherein $R_1$ is benzyl or 1-phenylethyl.

4. The process according to claim 1, Therein $R_1$ is benzyl and reductive amination produces compound (II) in racemic form, and the process further comprises resolving the racemic compound (II) with a chiral acid, to form the corresponding acid addition salt of compound (II), and wherein the chiral acid is (S)-mandelic acid.

5. The process according to claim 1, wherein $R_1$ is 1-phenylethyl, and compound (VIII) is (R)-phenylethylamine.

6. The process according to claim 1, wherein reductive amination is carried out in the presence of a solvent selected from an organic solvent, an aqueous solvent or a mixture thereof.

7. The process according to claim 1, wherein the molar ratio of the compound of formula (II) to the compound of formula (III) in step (ii) ranges from about 1.5:1.

8. The process according to claim 1, wherein the condensation in step (ii) is carried out in the presence of a solvent selected from the group consisting of methanol, ethanol, isopropyl alcohol (IPA), t-butanol, methyl isobutylketone, acetone, methyl ethyl ketone, n-butanone, toluene, t-amylalcohol, acetonitrile, diglyme, THF, DMSO, xylene and HMPA; a base selected from triethylamine, potassium carbonate, sodium carbonate and diisopropylamine and a catalyst selected from the group consisting of potassium iodide, sodium iodide, tetrabutyl ammonium bromide, 18-crown 6 ether, tetrabutyl ammonium sulphate and tetrabutyl ammonium iodide.

9. The process according to claim 1, wherein the chiral oxazaborolidine catalyst is selected from the group consisting of cis-(1R,2S)-aminoindanol, R-diphenyl prolinol, R-methyl oxazaborolidine derived from R-diphenyl prolinol, trimethylboroxine and methyl boronic acid and non-α-substituted (R)-indoline-2-carboxylic acid.

10. The process according to claim 1, wherein the reduction in step (iv) is carried out by a hydrogen donating compound in the presence of a hydrogen transfer catalyst.

11. The process according to claim 1, wherein the reduction in step (iv) is carried out by a hydrogen donating compound in the presence of a hydrogen transfer catalyst, and the reduction is carried out in a solvent selected from an alcohol or dioxane.

12. The process according to claim 1, wherein the reduction in step (iv) is carried out by a hydrogen donating compound in the presence of a hydrogen transfer catalyst, and the hydrogen transfer catalyst is on a support of solid materials selected from alumina, silica gel or clay.

13. The process according to claim 1, wherein the reduction in step (iv) is carried out by ammonium formate using a hydrogenation catalyst, and the hydrogenation catalyst is selected from palladium, platinum, ruthenium or rhodium supported on carbon, clay, silica or alumina and is carried out in the presence of an inert solvent selected from methanol, ethanol, isopropyl alcohol or butanol, acetonitrile, DMF (Dimethylformamide), DMSO or THF.

14. A process for preparing the (R,R) diastereomer of formoterol or a pharmaceutically acceptable salt thereof, the process comprising preparing the compound of formula (VI) according to claim 1, and converting the compound of formula (VI) to the (R,R) diastereomer of formoterol.

15. The process according to claim 14, wherein the conversion comprises formulating the compound of formula (VI) in formic acid and acetic anhydride to produce a compound of formula (VII)

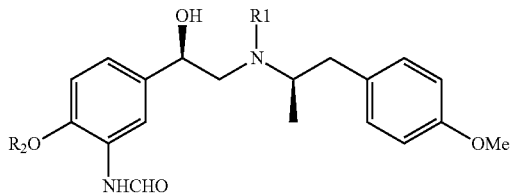

(VII)

wherein the compound of formula (VII) is isolated in the form of an acid addition salt thereof as a compound of formula (VIIa)

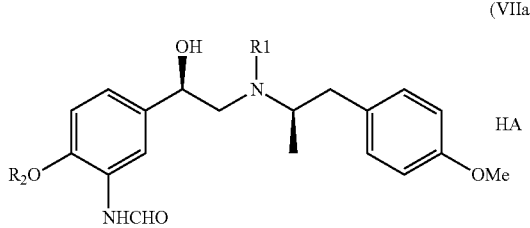

(VIIa)

and wherein $R_1$ and $R_2$ are independently optionally substituted arylalkyl and $A^-$ is an anion.

16. The process according to claim 15, wherein the process further comprises converting the compound of formula (VII) to the corresponding (R,R) diastereomer of formoterol (I), wherein the conversion to (R,R)-formoterol comprises deprotecting the $NR_1$ and $OR_2$ groups by hydrogenolysis of the compound of formula (VII) with hydrogen gas in the presence of a noble metal catalyst selected from the group consisting of palladium, palladium hydroxide, palladium on activated carbon, palladium on alumina, platinum, platinum on activated carbon and Raney nickel, and wherein the deprotection of the compound of formula (VII) is carried out in the presence of a solvent selected from the group consisting of an alkyl acetate, a $C_1$ to $C_6$ alkylamine, an alcohol, an aliphatic hydrocarbon, an aromatic hydrocarbon, a heterocycle, a diallylether, an acid, a mixture of water and a water miscible solvent, an ionic liquid, a halogenated solvent and mixtures thereof.

17. The process according to claim 14, wherein the (R,R)-formoterol is converted to a pharmaceutically acceptable salt thereof.

18. The process according to claim 1, wherein the reductive amination is carried out at a temperature of −10 to 30° C.

* * * * *

UNITED STATES PATENT AND TRADEMARK OFFICE
CERTIFICATE OF CORRECTION

PATENT NO. : 9,029,421 B2
APPLICATION NO. : 12/995016
DATED : May 12, 2015
INVENTOR(S) : Vaishali Vaman Haldavanekar et al.

Page 1 of 1

It is certified that error appears in the above-identified patent and that said Letters Patent is hereby corrected as shown below:

In the Claims:

Claim 4, Column 24, Line 7, replace "claim 1, Therein" with --claim 1, wherein--.

Claim 15, Column 25, Line 2, replace "formulating the compound" with --formylating the compound--.

Claim 16, Column 28, Line 18, replace "a diallylether" with --a dialkylether--.

Signed and Sealed this
Twenty-ninth Day of September, 2015

Michelle K. Lee
*Director of the United States Patent and Trademark Office*